United States Patent
Lande (10) Patent No.: US 11,878,097 B2
(45) Date of Patent: Jan. 23, 2024

(54) VACUUM ASSISTED SELF-PRIMING HEART LUNG MACHINE IN A BOX

(71) Applicant: Arnold J. Lande, Northport, MI (US)

(72) Inventor: Arnold J. Lande, Northport, MI (US)

( * ) Notice: Subject to any disclaimer, the term of this patent is extended or adjusted under 35 U.S.C. 154(b) by 0 days.

(21) Appl. No.: 17/727,175

(22) Filed: Apr. 22, 2022

(65) Prior Publication Data

US 2022/0378991 A1 Dec. 1, 2022

Related U.S. Application Data (60) Provisional application No. 63/193,037, filed on May 25, 2021.

(51) Int. Cl.
| | | |
|---|---|---|
| *A61M 1/14* | (2006.01) | |
| *B65D 17/28* | (2006.01) | |
| *B65D 81/20* | (2006.01) | |

(52) U.S. Cl.
CPC ........ *A61M 1/1522* (2022.05); *A61M 1/1562* (2022.05); *A61M 1/1565* (2022.05); *B65D 17/4011* (2018.01); *B65D 81/2007* (2013.01)

(58) Field of Classification Search
CPC .......... A61M 2209/00; A61M 2209/06; A61M 2209/08; A61M 25/002; A61M 5/002; B01D 63/14; B65D 17/4011; B65D 81/2015; B65D 81/3888; B65D 81/3862; B65D 81/3851; B65D 85/00; A61J 1/20
See application file for complete search history.

(56) References Cited

U.S. PATENT DOCUMENTS

| | | | |
|---|---|---|---|
| 3,396,849 A | 8/1968 | Lande | |
| 5,753,173 A | 5/1998 | Leonard et al. | |
| 6,468,473 B1* | 10/2002 | Lindsay | A61M 1/3621 604/4.01 |
| 9,878,821 B2* | 1/2018 | Sibley | B65B 31/00 |
| 2020/0156852 A1* | 5/2020 | Veiseh | B65D 81/3816 |
| 2022/0331503 A1* | 10/2022 | Koenig | A61M 1/369 |

FOREIGN PATENT DOCUMENTS

| | | |
|---|---|---|
| CN | 211024414 U | 7/2020 |
| CN | 211512853 U | 9/2020 |
| JP | 2009106445 A | 5/2009 |
| WO | 0047266 A1 | 8/2000 |

OTHER PUBLICATIONS

Notification of Transmittal of the International Search Report and the Written Opinion of the International Searching Authority, or the Declaration; International Search Report; and Written Opinion of the International Search Authority for corresponding PCT Patent Application No. PCT/US2022/029211, dated Aug. 30, 2022, 8 pages.

* cited by examiner

*Primary Examiner* — Erich G Herbermann
*Assistant Examiner* — Quynh Dao Le
(74) *Attorney, Agent, or Firm* — Brad J. Thorson; DeWitt LLP (57) ABSTRACT

The availability of a heart-lung machine in a box provides an opportunity for saving lives in emergency situations arising outside a hospital and for more cost effective care in hospital settings.

8 Claims, 10 Drawing Sheets

VACUUM ASSISTED SELF-PRIMING HEART LUNG MACHINE IN A BOX

CROSS-REFERENCE TO RELATED APPLICATIONS

This application is a non-provisional application of Application No. 63/193,037, filed May 25, 2021, and claims priority from that application which is also deemed incorporated by reference in its entirety in this application.

STATEMENT REGARDING FEDERALLY SPONSORED RESEARCH OR DEVELOPMENT

Not applicable

BACKGROUND OF THE INVENTION

I. Field of the Invention

The present invention relates generally to a medical apparatus for treating patients suffering from cardiovascular pulmonary deficiency and, more particularly, to a heart-lung machine that is highly portable, self-priming and readied for use to treat a patient by opening its container allowing ambient air to be rapidly admitted. The heart-lung machine may also be referred to and used as an ECMO system.

II. Discussion of the Prior Art

It is well known in the medical literature that ECMO systems can be employed in treating severe hypoxemic respiratory failure and cardiogenic shock.

There are two types of ECMO systems, Veno-venous for respiratory support (VVECMO) and Veno-arterial for cardio-respiratory support (VAECMO). In VVECMO, blood is accepted from a patient's vein, is oxygenated, $CO_2$ is removed, and the blood is returned via a vein, to the patient's right atrium. A minimal strength pump is required for this to work, and the patient must have cardiac function. For VVECMO, blood from a vein is run through a blood oxygenator and returned to a vein. For VAECMO, blood is taken from a vein and is returned to an artery with a pump required. An ECMO system circuit comprises a reservoir, a blood oxygenator, a pump, and heat exchanger that are connected in a series circuit by plastic tubing. Before the circuit can be connected to a patient, it is imperative that all air be removed from the circuit before it is connected to cannulas that access the patient's circulatory system. This operation of driving air from the ECMO circuit is referred to as priming and it involves circulating normal saline through the ECMO circuit to ensure that air cannot enter the patient's blood stream. In a hospital setting, prior art ECMO systems undergo priming by a perfusionist aided by one or more technicians.

The present invention provides a way of packaging a heart-lung/ECMO circuit, which at this point is dry, in a container so it may be stored, ready for use, over prolonged periods of time and when needed for patient treatment, the heart-lung/ECMO circuit, including a pump, a blood oxygenator, the blood temperature regulator (heater), the blood reservoir and the associated interconnecting tubing is automatically primed upon opening of the container.

SUMMARY OF THE INVENTION

The foregoing self-priming feature is provided by a sealable container in which an insert is provided. The insert comprises a pressure protective, rigid, hollow, open cell foam packing material, that is contained within an outer gas impervious film sleeve. The ECMO/heart-lung machine circuit is housed within this hollow foam protective insert within a flexible bag containing everything except the priming fluid located within the outer sealable container. Also, exterior to the pressure protective inner foam insert and connected through a pressure activated valve, is a length of tubing leading to an input line of the ECMO/heart-lung machine circuit.

At the time of manufacture of the above-described packaging arrangement, the outer and inner containers are first flushed with $CO_2$ to exhaust all $N_2$ from the container which is then vacuum-sealed such that all the contents of the outer vacuum can are at a predetermined pressure less than atmospheric. Likewise, the interior of the open cell, space filling plastic foam housing containing the ECMO/heart-lung machine circuit is at the same negative pressure such that there is no tendency for the priming fluid to be displaced from its bag into the circuit. However, upon subsequently opening the outer container, atmospheric pressure presses on the flexible bag of priming fluid while the inner housing, at least momentarily, remains at its negative pressure causing the priming fluid to be forced by atmospheric pressure from its bag and through the ECMO/heart-lung machine circuit in the still evacuated open cell foams packing inner housing to displace all air that may have been present in the ECMO/heart-lung machine circuit. The primed ECMO/heart-lung machine circuit is now ready to be connected to the patient. With the actuation of the pump and the patient's own veinous pressure, blood will be made to flow through the circuit such that oxygen will be picked up by hemoglobin cells while $CO_2$ is released therefrom via the system's blood oxygenator.

Additionally, the pump which can be electrically powered or powered manually is arranged to draw (pull) blood through the originator rather than push blood through the oxygenator. This feature and other features of the preferred embodiment essentially eliminate the risk of air bubbles forming that could result in an embolism.

Those skilled in the art will also recognize that additional force may be placed on the priming fluid bag upon opening of the outer container by either squeezing the bag or elevating it on an IV bag support pole if one is available.

BRIEF DESCRIPTION OF THE DRAWINGS

The foregoing features, objects and advantages of the invention will become apparent to those skilled in the art from the following detailed description of the preferred embodiment, especially when considered in conjunction with the accompanying drawings in which like numerals in the several views refer to corresponding parts.

DESCRIPTION OF THE PREFERRED EMBODIMENT

This description of the preferred embodiments is intended to be read in connection with the accompanying drawings, which are to be considered part of the entire written description of this invention. In the description, relative terms such as "lower", "upper", "horizontal", "vertical", "above", "below", "up", "down", "top" and "bottom" as well as derivatives thereof (e.g., "horizontally", "downwardly", "upwardly", etc.) should be construed to refer to the orientation as then described or as shown in the drawings under discussion. These relative terms are for convenience of description and do not require that the apparatus be constructed or operated in a particular orientation. Terms such as "connected", "connecting", "attached", "attaching", "join" and "joining" are used interchangeably and refer to one structure or surface being secured to another structure or surface or integrally fabricated in one piece, unless expressively described otherwise.

The named inventor was previously granted U.S. Pat. No. 3,396,849. That patent discloses a liquid-gas, or liquid-liquid, heat exchange device utilizing a permeable membrane or other thin sheet. Such a device has been used for oxygenating and pumping blood in an extra or intracorporeal circulation system for temporarily assuming or assisting the functions of the heart and lungs in a human being or other animal, or for use as an artificial kidney or liver or heat exchanger. The device included a means for supporting and manifolding multiple short parallel films of blood between ultra-thin permeable membranes or other films for exposure to an oxygenating gas or dialysis liquid or heating or cooling medium through the membrane or other film.

Broadly stated, the membrane fluid exchange device of the above-referenced patent comprised a plurality of stacked generally flat rigid membrane support plates, spacer means to hold each adjacent pair of plates closely spaced apart, a thin membrane, either permeable or not depending upon use of the device, disposed between each plate and each spacer, each plate having a plurality of projections to hold the membrane spaced from the surface of the plate, means for introducing one fluid for flow as a thin film in one direction between the two layers of membrane between each adjacent pair of plates, and means for introducing another fluid for flow in either the same or the opposite direction through the space between each membrane support plate and the adjacent membrane layer.

By way of background, the first workable artificial kidney was developed in the 1940s. This device consisted of a long cellophane sausage casing through which the blood passed, and which was wound as a spiral about a central support. Subsequent models later in wide use were wound layer upon layer over a central core. Because the resistance to blood flow over the 25 foot or so length of this casing is high, it is necessary to wind the sausage casing loosely to permit a relatively thick film of blood to bring the resistance of the device down to a reasonable level. This coiled tubing is immersed in a dialysis liquid. Whereas the dialysis liquid had to pass only a few inches up between the winding of the sausage casing, the blood had to travel the full distance of about 25 feet around and around from the center of the coil to the periphery. For many years, this device was the most generally used unit for hemodialysis. It had the advantage that it can be manufactured for a single use and then disposed of. It has the disadvantage of requiring a relatively large volume of donor blood to initially fill the artificial kidney. Safe operation required close attention and much time. A large amount of dialysate was required, and the unit was relatively expensive. Devices utilizing shorter flow paths were available, but require laborious disassembly, cleaning, sterilizing, and reassembly after each use.

As described in the above-referenced patent, in the related area of blood oxygenation, membrane oxygenators for use during cardiac surgery had been proposed. The devices then available never found wide acceptance. Instead, versions of the bubble oxygenator and film oxygenators continued to dominate the field, although there were numerous indications that the separation of blood and oxygen by a permeable membrane, as in the lungs, is much less traumatic to several components of blood. The membrane oxygenators then in use had been subject to disadvantages like those of the artificial kidney.

The invention described in U.S. Pat. No. 3,396,849 is directed to fulfilling the acute need for a low priming volume disposable membrane oxygenator-dialyzer. This unit is characterized by an elongated permeable membrane of extreme thinness and great strength, pleated, and alternating between a plurality of rigid membrane supports stacked together into a compact assembly ⅕ the size of any similar unit previously envisioned. The pleated membrane allows for manifolding blood and oxygen or dialysis fluid into parallel thin films without potential mixing. The device is characterized by truly uniform blood film thickness, by the rigid membrane support components, and by elimination of any possibility of short circuiting or leaking.

The invention described in U.S. Pat. No. 3,396,849 is illustrated in the Figures of that patent which are reproduced herein as FIGS. 1-13. It will be seen from FIGS. 1-13 that the oxygenator-dialyzer unit, indicated generally at 10, is a compact block-life structure encasing a plurality of stacked membrane supports and spacers around which a permeable membrane is pleated, as described in greater detail below. For convenience, the unit will be described with reference to oxygenation of blood as practiced during cardiac surgery, although it will be understood that the same structure is utilized in an artificial kidney and other uses.

The oxygenator includes a blood inlet 11 which communicates directly with an internal channel 12 which functions as a manifold to distribute the blood along the length of the oxygenator unit and which in turn communicates with channels in the edges of the membrane supports, as further described below. The unit is provided with a blood outlet 13 which communicates directly with an internal collector channel 14 which collects the oxygenated blood by communicating with outlet channels in the edges of the membrane support members.

Figures 3, 4:
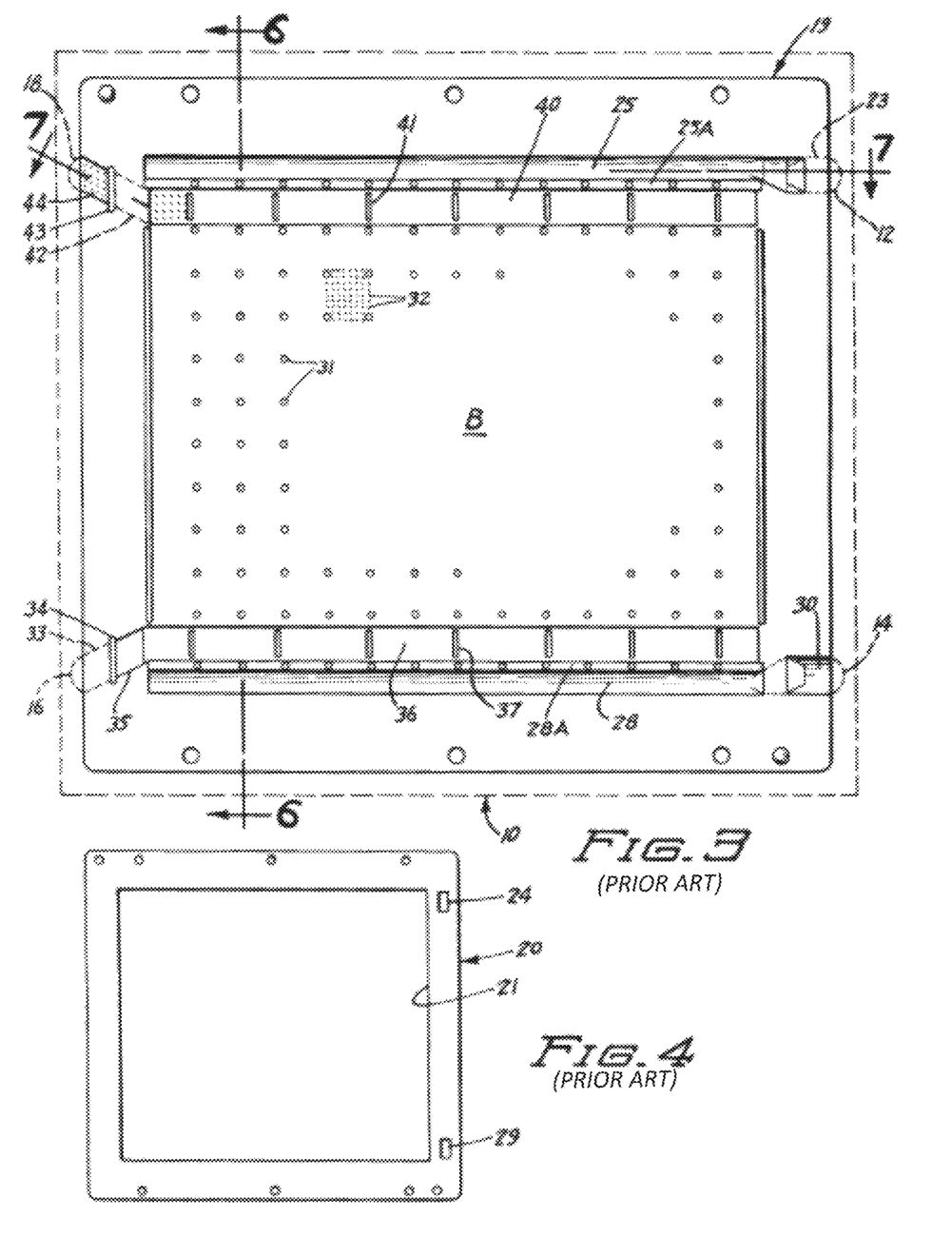
FIG. 3 is a similar plan view on an enlarged scale of the opposite side (face B) of one of the rigid membrane supports of the prior art compact small rigid membrane oxygenator-dialyzer of FIG. 1, shown with its housing or casing in broken lines.
FIG. 4 is a plan view on a reduced scale of a spacer component inserted between the membrane supports of the prior art compact small rigid membrane oxygenator-dialyzer of FIG. 1.
Figure 5:
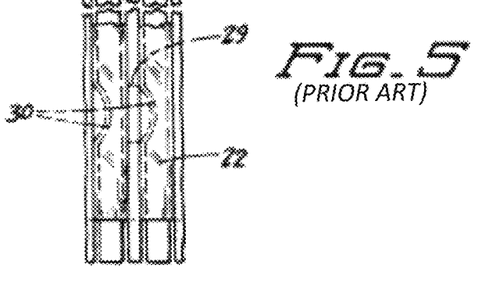
FIG. 5 is a greatly enlarged fragmentary end elevation of a set of membrane supports and spacer of the prior art compact small rigid membrane oxygenator-dialyzer of FIG. 1.
Figure 6:
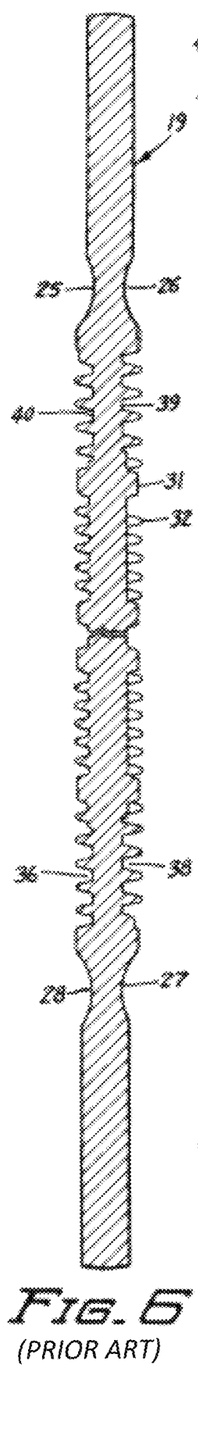
FIG. 6 is a greatly enlarged section on the line 6-6 of FIG. 3 and in the direction of the arrows.

The oxygenator also includes an oxygen inlet 15 which communicates with an internal channel 16 (FIG. 3) which functions as a manifold for distribution of oxygen along the length of the unit and a carbon dioxide outlet 17 which in turn communicates with an internal $CO_2$ collector channel 18 (FIG. 3). The internal channels 16 and 18 connect to channels in the membrane supports. As illustrated, the gas flow is countercurrent to the blood flow, but optionally the blood and gas may flow in the same direction.

Figure 1:
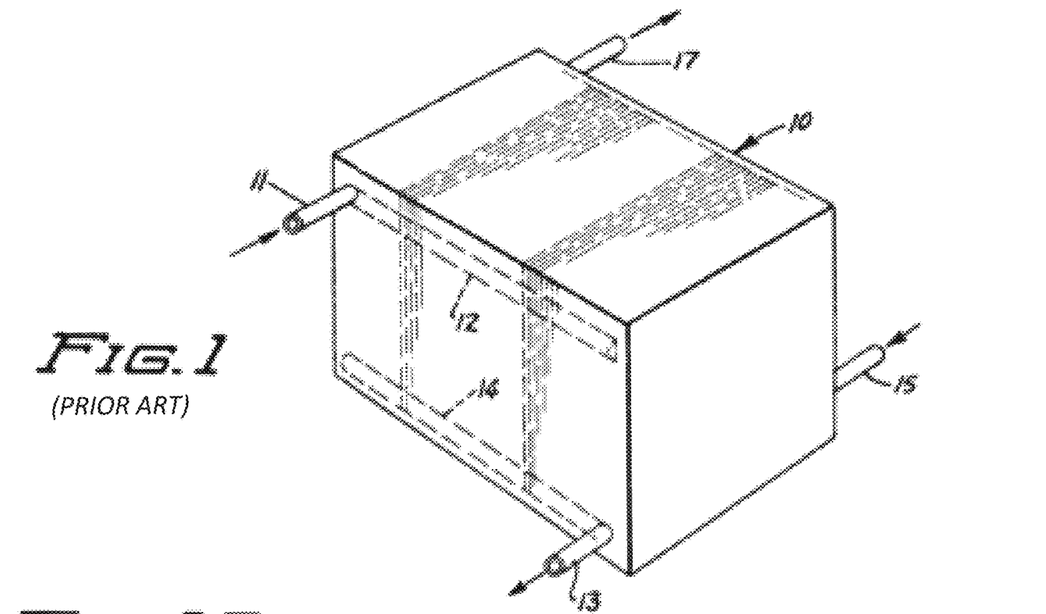
FIG. 1 is an isometric view of a prior art compact small rigid membrane oxygenator-dialyzer.
Figure 2:
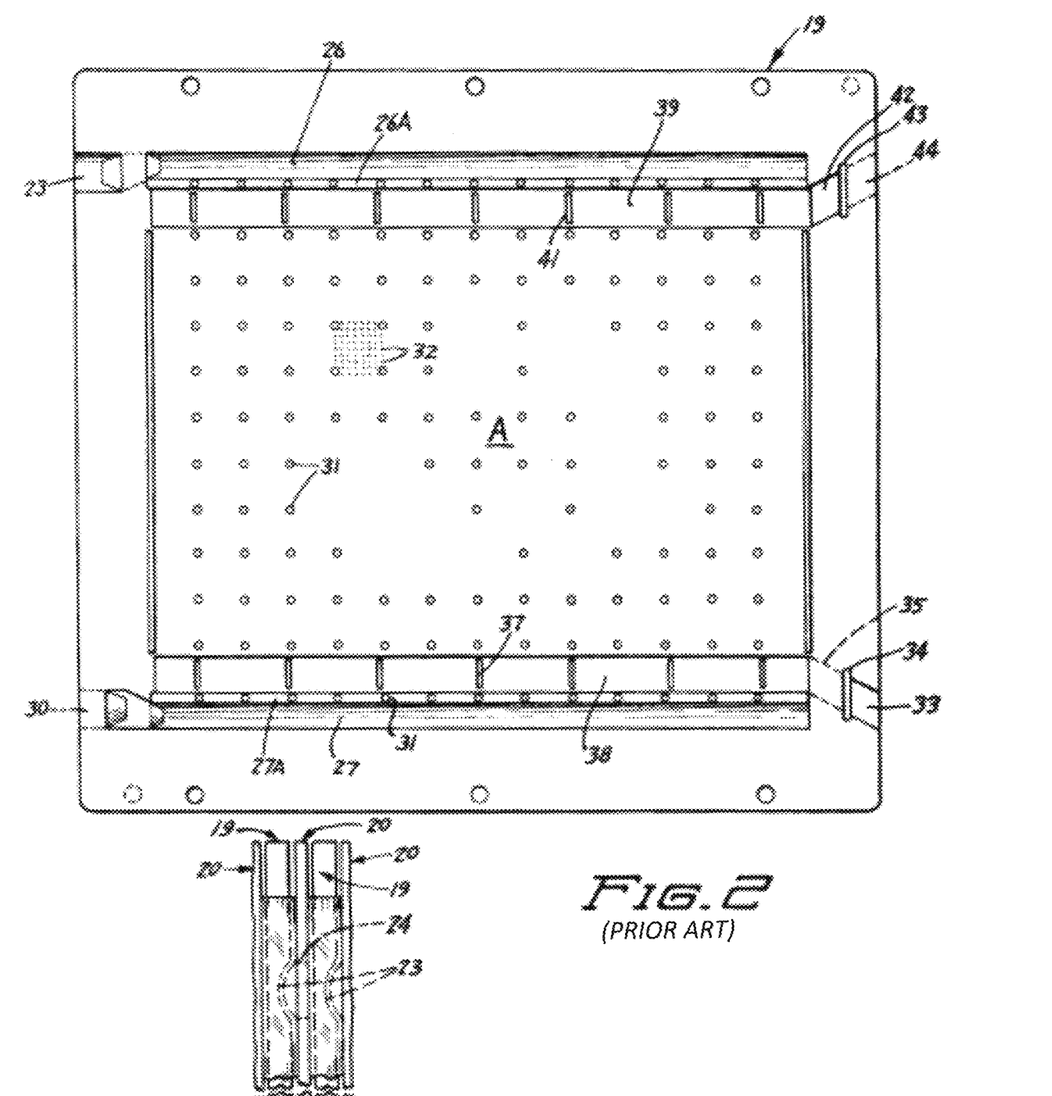
FIG. 2 is a plan view on an enlarged scale of one side (face A) of one of the rigid membrane supports of the prior art compact small rigid membrane oxygenator-dialyzer of FIG. 1.

Referring now to FIGS. 2 and 3 there is shown in detail the structure of the membrane support components of the oxygenator. The membrane supports, indicated generally at 19, are in the form of rigid rectangular generally flat plates whose opposite faces are molded to form cavities which define flow channels and to form membrane support elements. As one example, each plate may be about 3.5 by 3 inches and about 5 to 1 inch thick. The edges of each plate frame a central working area which may be, for example, about 2 by 3 inches. The spacer member indicated generally at 20 and shown in FIG. 4 has the same outside dimensions as the support plates 19 and frames an opening 21 of the same size as the overall working area of the membrane support plates.

Because the repeating functional unit of the oxygenator device is composed of a pair of membrane support plates 19 disposed in face-to-face relation with a spacer member 20 in between, this can best be visualized by considering FIGS. 2 (face A) and 3 (face B) in side-by-side relation as the pages of a book and adapted to be closed on one another in the same manner but with the spacer member of FIG. 4 interposed and with a thin flexible permeable membrane 22 interposed between one face of each of the membrane support plates and each face of the spacer. The blood flow is always between the two membrane surfaces embracing the spacer 20, but the membrane is extremely thin, resilient, and deformable and is forced by pressure of the blood into certain of the cavities in the faces of the plates 19 so that those cavities define channels between the membrane which guide and direct the flow of blood. The blood is at no time in direct contact with the membrane support plates.

Face A of each support plate 19 thus includes a short edge cavity or recess 23 the inner end of which is disposed to be in registry with one end of an opening 24 in spacer 20. The opposite end of opening 24 is then disposed to be in registry with the end of a narrow, elongated cavity 25 extending across the top on the opposing face B of the adjacent facing support plate. A mating cavity 26 extends across the top of the first face (face A, FIG. 2) of the support plate. The elongated channel formed between the opposing faces when the two plates are stacked provides a space in which the thin flexible membrane may be deformed outwardly under pressure of flowing blood and so form the membrane into a channel through which the blood is distributed.

A corresponding pair of cavities adapted to define a blood collection channel are disposed across the bottom of the membrane support plate, cavity 27 being on one face (face A, FIG. 2) and cavity 28 being on the opposite face (face B, FIG. 3). One end of cavity 27 lies in registry with one end of an opening 29 in spacer 20 in the assembled unit and the opposite end of opening 29 is disposed to be in registry with the inner end of a recess 30 in facing membrane support plate (FIG. 3) and defining a short blood outlet channel. Again, blood does not flow through the channel created between cavities 27 and 28, but between the channel formed in the flexible membrane distended to fill out that cavity. The blood inlets defined by recesses 23 communicate with the manifold channel 12 extending the length of the assembled oxygenator unit (FIG. 1) adjacent the top edge and the blood outlet defined by recesses 30 communicate with the collection channel 14 disposed along the length of the oxygenator unit along the bottom edge.

Figures 7, 8, 9:
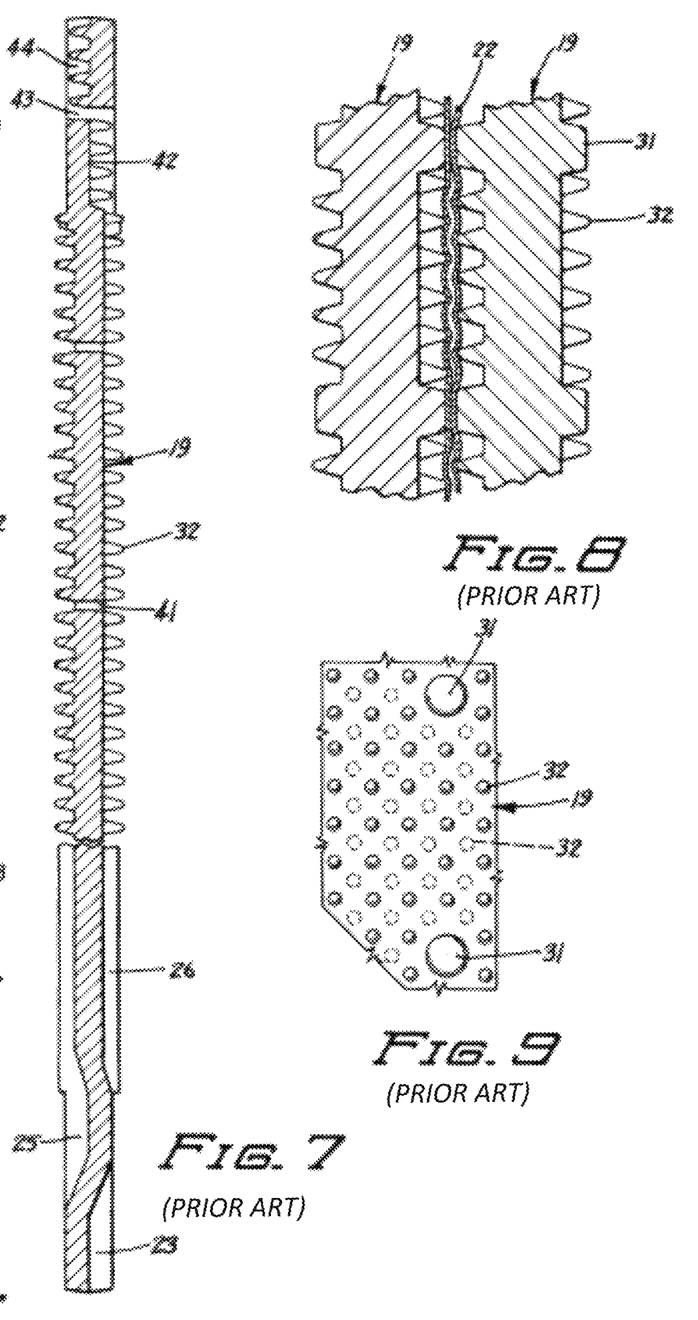
FIG. 7 is a greatly enlarged section on the line 7-7 of FIG. 3 and in the direction of the arrows.
FIG. 8 is a fragmentary section, further enlarged, showing the manner of support of the membrane between two adjacent membrane supports of the prior art compact small rigid membrane oxygenator-dialyzer of FIG. 1.
FIG. 9 is a greatly enlarged fragmentary plan view showing the arrangement of the myriad of individual membrane supporting elements of the rigid membrane supports of the prior art compact small rigid membrane oxygenator-dialyzer of FIG. 1.

Between cavities 25-26 and cavities 27-28 the opposite sides of the folded flexible membrane 22 are supported by a plurality of evenly spaced and mated pedestals 31 and a myriad of Bleumle cones 32 disposed between the several pedestals. The cones 32 are evenly spaced but are off-set as between one face of the support plate and the other, as best seen in FIGS. 8 and 9. Adjacent each cavity 25-28 there is a slight ridge 25A-28A on the side toward the cone field. The blood flows under low resistance through the channels formed between the facing cavities. The resistance ridges cause a higher resistance flow through the spaces between the pedestals. Because of the vast number of cones on each side of each membrane support, for convenience only a few of these are shown. It will be understood, however, that on membrane support plates of the size indicated there are 156 pedestals and approximately 7000 cones on each side.

The face-to-face mating pedestals insure constant spacing between the membrane surfaces, the amount of spacing being related to the height of the pedestals and the thickness of the spacer member. The cones rigidly support the membrane on both sides at myriad points. The cones at the blood inlet end along the top of each membrane support plate where the pressure of the blood is greatest, are desirably about 0.002 inch slightly higher than at the other end to make maximum utilization of countercurrent flow possible by providing constant fluid film thickness even with the exaggerated pressure drops encountered during countercurrent flow. The blood flow is retained between the two surfaces of the pleated membrane, supported all the time by the cones and pedestals.

The oxygen circulates through the spaces between the membrane and the membrane supports in either the same direction or, as illustrated, in countercurrent flow. Each membrane support plate 19 in the edge on the side opposite from the blood inlet and outlet recesses is provided with a short shallow oxygen inlet channel 33 which communicates with a narrow slot 34 or similar opening leading a short shallow channel 35 on the opposite face of the plate. Channel 35 leads directly to a shallow elongated oxygen distribution channel 36 which extends across the width of plate 19 adjacent the bottom edge parallel to and immediately adjacent to recess 28 defining the blood collection channel. A plurality of narrow slots 37 or similar openings through the plate communicate with a corresponding shallow oxygen distribution channel 38 on the opposite face of plate 19. This permits uniform distribution of the oxygen introduced through channel 33 on both sides of membrane support plate 19.

The gas is passed under pressure through the myriad passages between the cones 32 and pedestals 31 between the outer surface of membrane 22 and the face surface of the membrane support plate. The exchange of oxygen for carbon dioxide in the blood takes place through the exposed membrane surface. The carbon dioxide is forced by the flow of oxygen on through the space between the membrane and membranes support plate to a pair of shallow $CO_2$ collection channels 39 and 40 on opposite sides of the plate extending across the top, parallel to and adjacent to the recesses 25 and 26 defining the blood distribution channel. The $CO_2$ collection channels communicate through a plurality of slots 41 or similar openings. One end of channel 39 communicates directly with a short discharge channel 42 which in turn communicates through a slot 43 or similar opening with a discharge recess or channel 44.

Oxygen inlet channels 33 communicates with an oxygen distribution channel or manifold 16 extending lengthwise of the assembled oxygenator unit and communicating with each of the assembled plate, membrane, and spacer units. Similarly, $CO_2$ discharge channels 44 communicate with a $CO_2$ collection channel 18 extending lengthwise of the oxygenator unit and discharging through outlet 17. Channels 33, 35, 36, 38, 39, 40, 42 and 44 are preferably all provided with cones 32 to support the membrane 22 away from the plate surface to facilitate free flow of gas through the unit. Resistance ridges are also desirably provided adjacent each of channels 36, 38, 39 and 40 between the channels and main cone field.

It will be noted that the passage of blood through slots 24 and 29 in spacer 20 from one side of the spacer to the other and passage of gas through slots 34 and 43 from one side of plate 19 to the other ensures that the border of each face of membrane support plate 19 presents a continuous flat planar surface surrounding the working area of each face of said plate. This ensures that when membrane is disposed over each face of membrane support plate 19 and overlaid with the flat planar surface of spacer 20 and slightly compressed in assembly, the membrane functions as a gasket to insure a leakproof assembly.

Figure 10:
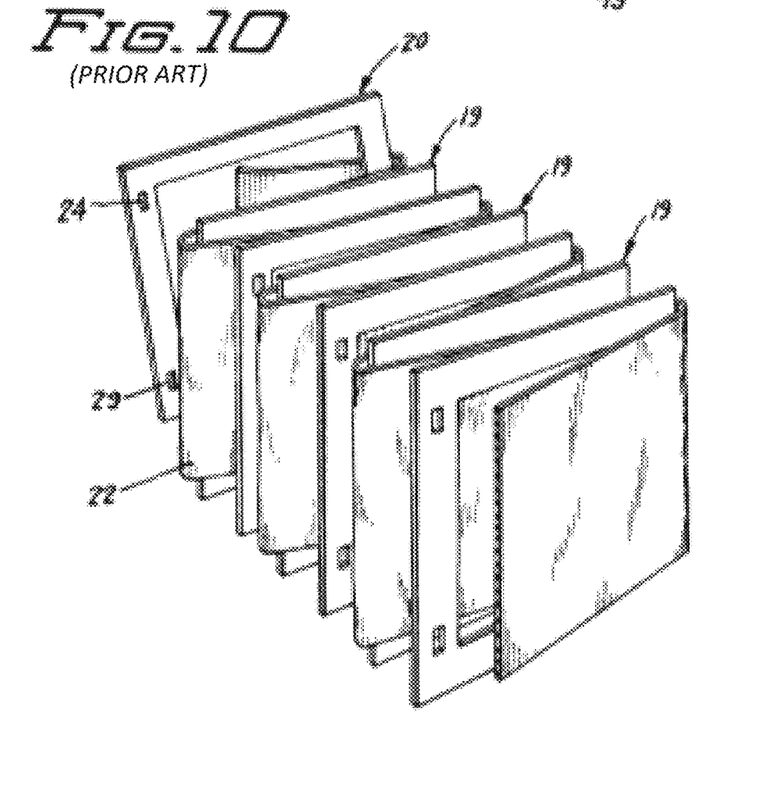
FIG. 10 is a perspective schematic illustration of the manner in which the membrane supports and spacers of the prior art compact small rigid membrane oxygenator-dialyzer of FIG. 1 are assembled.

The way the components are assembled into an oxygenator is shown in FIG. 10. Membrane supports 19 are alternated with spacers 20. The permeable membrane 22 is disposed in an Esmond pleat passed in a circuitous path to provide a membrane layer between the faces of each adjacent pair of components. The membrane passes over the membrane supports 19 around the end containing the blood inlet and outlet recesses 23 and 39 and extends around the spacers 20 at the edge opposite from that including the passages 24 and 29. In this manner the blood flow recesses 23 and 30 are exposed on one side of the assembled unit for communication with channels 12 and 14, respectively, and gas flow recesses 33 and 44 remain exposed on the opposite side of the assembled unit for communication with channels 16 and 18. The assembled unit need not be, but if desired may optionally be suitably encased, as in silicone rubber or the like, or otherwise enclosed in a housing.

Membrane 22 must be thin and flexible. For oxygenation it must be permeable to the passage of gases, such as oxygen and carbon dioxide, while remaining impermeable to the passage of liquids, such as blood. For dialysis, the membrane must permit diffusion of blood impurities by liquid-liquid exchange. One exemplary material for oxygenation was a three-ply laminated membrane of silicone rubber of approximately 1 mil thickness manufactured by the General Electric Company. For dialysis, cellophane or other conventional dialysis membranes may be used. For heat exchange metal foil, stainless steel or aluminum or the like, maybe used as the membrane.

Figure 11:
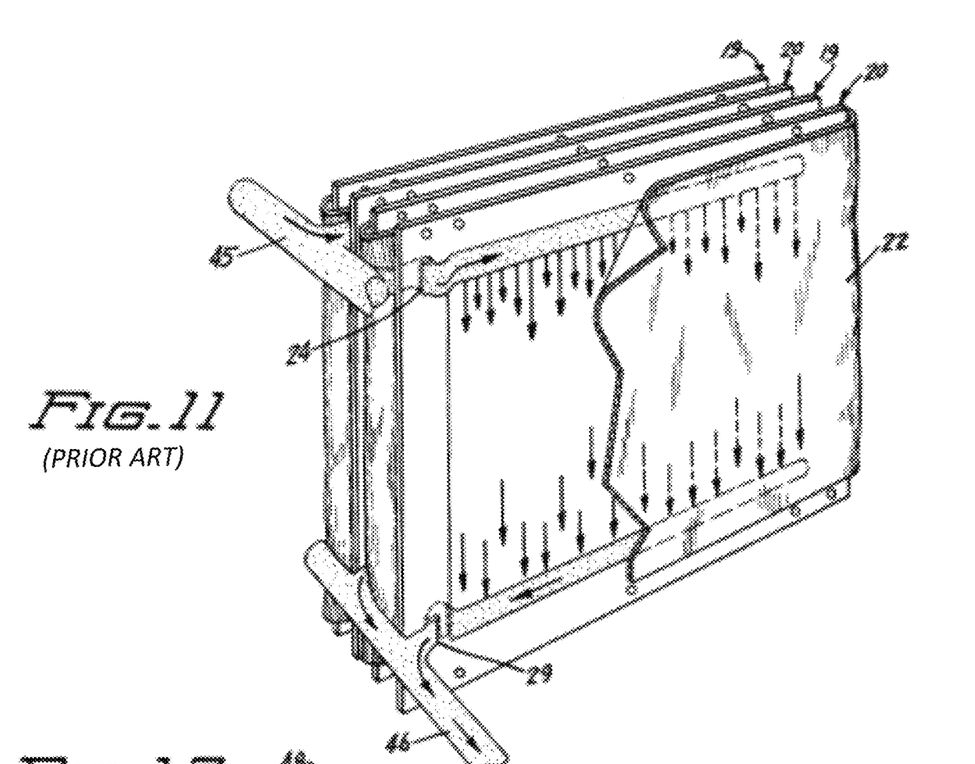
FIG. 11 is a fragmentary perspective view showing the components of the prior art compact small rigid membrane oxygenator-dialyzer of FIG. 1 in their assembled relationship but spaced widely apart, to illustrate the flow pattern of blood through the unit.
Figure 12:
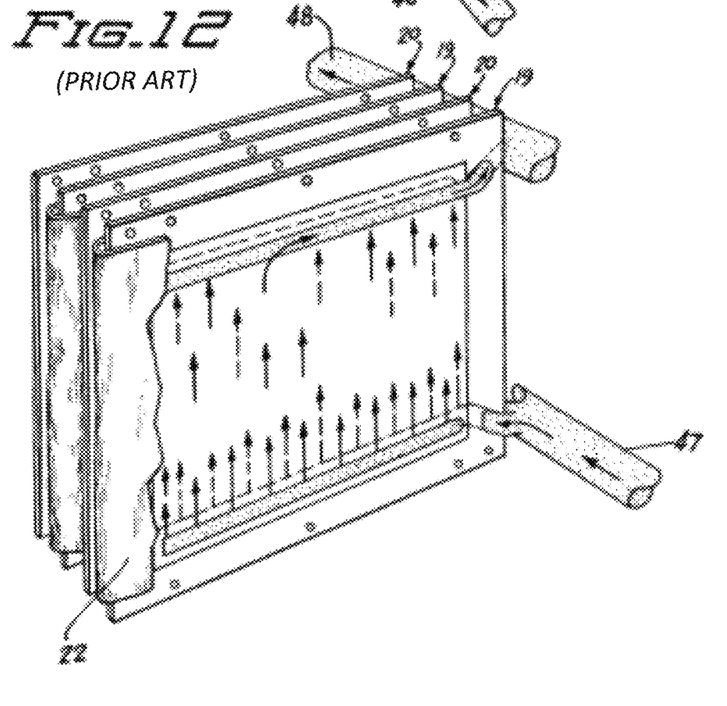
FIG. 12 is a similar view showing the flow of oxygen or dialysate through the of the prior art compact small rigid membrane oxygenator-dialyzer of FIG. 1.

The basic operation of the oxygenator unit according to the present invention is shown schematically in FIGS. 11 and 12. FIG. 11 shows the blood flow, while FIG. 12 shows countercurrent gas flow. As is understood, in a typical cardiac operation the patient's heart is first exposed and the two large veins at the right side of the heart which return the body blood to the heart are loosely looped with tape ready to be tied. Catheters to the great veins of the heart are inserted through a slit in the right atrium and a catheter to a systemic artery is inserted. The oxygenator is primed with the required amount of donor's whole blood or blood substitute, which in this instance is minimal. The tube from the veins of the patient passes through a standard blood pump and is connected to the blood inlet tube 11 of the oxygenator. The blood discharge tube 13 is connected through a similar standard blood pump to return the oxygenated blood to the patient. The device may also be used under non-operative circumstances utilizing peripheral veins and arteries over extended periods of time without the necessity of opening the chest.

With the oxygenator thus connected to the circulatory system of the patient, the blood pumps are turned on and the tapes looping the blood vessels are tightened. The heart, still beating, emptied of blood. The venous blood then, instead of going through the heart and lungs, passes through the blood pump into the blood inlet 11 of the oxygenator and flowed along the manifold channel 12 in a stream 45 indicated schematically in FIG. 11. This blood under pressure passes into the several blood inlet recesses 23, in the space between the spacer 20 and membrane 22 which is deformed by the blood pressure to fit into that recess.

Then the blood passes through passage 24 in each of the spacers 20 and into the elongated channel formed between the adjacent films of the pleated membrane defined by the cavities 25 and 26 of the facing surfaces of two adjacent membrane support plates 19, held slightly spaced apart by means of the spaced 20 and pedestals 31. The blood from that distribution channel flows as a thin film between the membrane surfaces, supported by the cones 32, as best illustrated in FIG. 8. During this passage, the thin film of blood is exposed on opposite sides through the membrane to oxygen and exchanges its carbon dioxide for oxygen.

The oxygenated blood is collected in a channel formed between the membrane films as distended to fit the cavities 27 and 28 in the same facing adjacent pair of membrane support plates. This stream of oxygenated blood 46 then passes out through passage 29 in spacer 20 and through the channel defined between recess 30 and the next adjacent membrane support plate and the spacer. These several streams of oxygenated blood, one from between each adjacent pair of membrane supports, is collected in the channel 14, discharged out through the outlet 13, and pumped back to the arterial system of the patient.

As seen schematically in FIG. 12, the oxygenation of the blood occurs as the result of contact through the membrane between the blood and oxygen introduced into the oxygenator in countercurrent flow. Thus, a stream of oxygen 47 is introduced into inlet 15 and distributed along the manifold 16 from which it has direct entry into the channels 33 in each of the membrane support plates 19. The oxygen then passes through slot 34, channels 35 and 36, slots 37 and channel 38 and thus is uniformly distributed on both sides of the membrane support in the spaces between the support surface and the membrane. During its passage through these spaces, in direction countercurrent to the simultaneous flow of blood between the supported membranes, the oxygen displaced part of the carbon dioxide in the blood and this mixture of carbon dioxide and oxygen is collected in channels 39 and 40, passing through slots 41, and out through channels 42, slot 43 and channel 44 to the $CO_2$ collector channel 18 and discharged through $CO_2$ outlet 17.

A unit as described in the aforementioned patent, with the dimensions given as exemplary, supports a half square meter of membrane and provides short (5 cm.) parallel 3-inch-wide blood flow paths, each of which is enclosed between two layers of membrane. Where greater capacity is needed, two or more assemblies may be used in parallel, or the unit may be assembled with a greater number of stacked plates. Although described with reference to oxygenation of blood it will be understood that the overall functioning of the device is generally similar when a dialyzing liquid is pumped in substitution for the oxygenating gas.

The same unit has potential for pumping blood. With the inclusion of two valves in the blood stream and pressure pulsation of the oxygen, a one-unit self-contained pump-oxygenator is possible. Such a unit may be implanted. The unit likewise has potential as an artificial liver. In this instance the blood stream of a healthy animal is routed through the channels otherwise used for oxygen or dialysate. The device may be used as a heat exchanger utilizing a film of extremely thin heat conductive material. Blood may be heated or cooled, or oxygen may be heated or cooled by using a suitable heating or cooling fluid flow on one side of the membrane.

Figure 13:
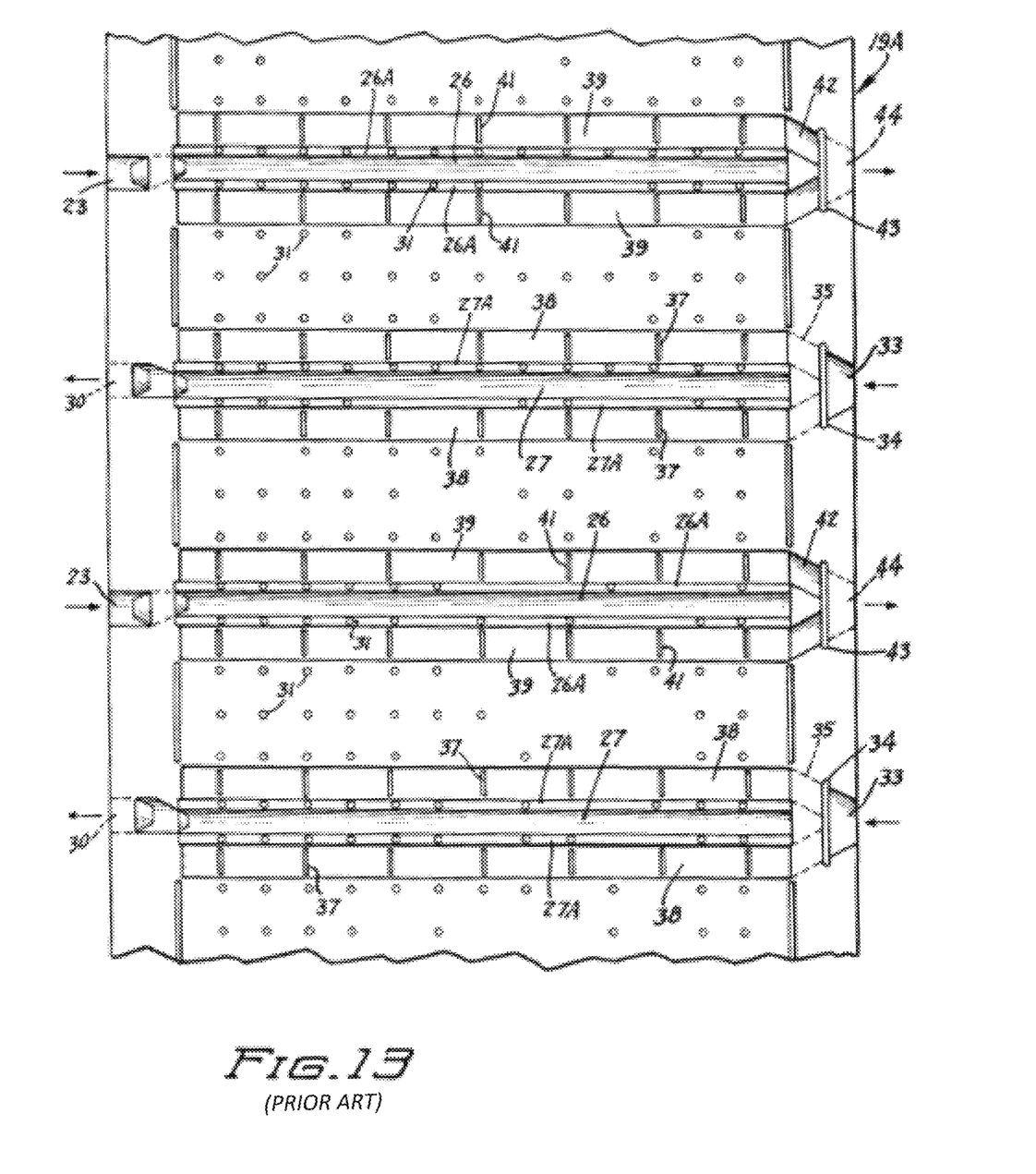
FIG. 13 is a greatly enlarged fragmentary plan view of a modified membrane support.

In FIG. 13 there is shown an alternative form of membrane support plate, indicated generally at 19A. The same component parts are correspondingly identified. One face of the plate 19A is provided with a plurality of recesses 23 and narrow elongated cavities 26. As already described, blood introduced through the channel defined by each recess 23 flows into an elongated channel defined by cavity 26 and a mating cavity in the next adjacent membrane support plate. According to the modified form of construction, the blood from that channel flows in two directions into one of two cone fields. The blood flow is over a shorter flow path and the blood is collected in a channel defined between one of a pair of elongated cavities 27 as shown and mating cavities in the next adjacent plate and discharges out through either one of blood outlet recesses 30.

The oxygen is introduced through inlet channels 33 and passes through slots 34 to channels 35 on the opposite side of the plate, generally in the manner already described. Then, the mixture of carbon dioxide and oxygen is collected for discharge out through a common discharge channel 44.

The overall construction of the gas distribution and collection channels and pedestal and cone fields are the same as already described except that the blood flow paths through the cone fields are shorter and there are multiple flow paths. The venous blood is introduced through one channel and the oxygenated blood from it is collected through two separate channels, whose flows are combined for circulation back to the body of the patient.

Desirably, the modified form of membrane support plate is constructed to provide a plurality of the functional units as illustrated in repeating pattern in each plate to provide for multiple flow of blood into and out of the space between each pair of adjacent plates with corresponding multiple inflow of oxygen and outflow of carbon dioxide and oxygen mixture. The overall functioning of the modified unit is identical, but the flow paths are materially shortened.

Figure 14:
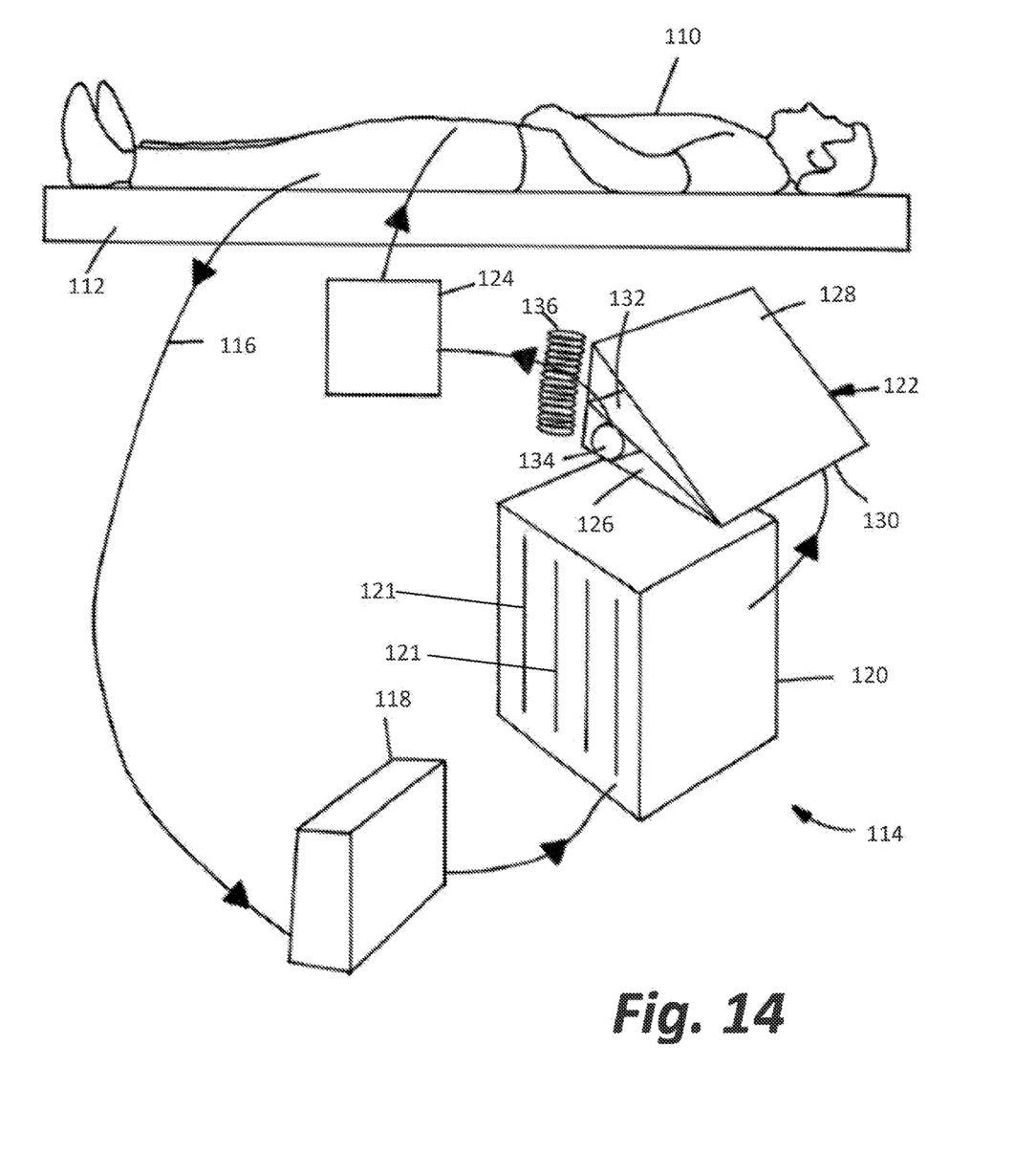
FIG. 14 depicts a patient on a bed to whom an ECMO/heart-lung machine circuit is attached.

With the foregoing background provided, a preferred embodiment of the present invention will now be described. Referring first to FIG. 14, shown is a patient 110 in a supine position on a bed or stretcher 112 with an ECMO/heart-lung machine circuit 114 (shown schematically) coupled to the patent. A bellows pump 122 causes blood from a suitable vein to flow through tubing 116 into a reservoir 118, then through a blood oxygenator 120, then through a heater module 124, and then back into a vein or an artery of the patient 110. Whether the blood is returned to the patient through a vein or artery may depend on whether VVECMO or VA ECMO is being applied.

Without limitation, the blood oxygenator 120 may comprise a device like that shown and described in the inventor's earlier U.S. Pat. No. 3,396,849, i.e., in FIGS. 1-13 and as described above with reference to those Figures.

However, as seen in FIG. 14, in the present invention the membranes 121 and the membrane support plates are oriented in a vertical plane instead of horizontally as in FIGS. 1-13. This helps ensure that microbubbles that may be present in the blood rise to the top and are eliminated from the oxygenated blood, namely, the blood flowing back to the patient.

The blood pump comprises first and second rigid plates 126, 128 hinged to one another along a line 130. An intermediate plate 132 divides the space between the plates 126, 128 into two pervious spaces, each of which is made to contain a collapsible bladder, as at 134, one of which becomes filled with blood to be pumped and the other fills with air, but preferably oxygen gas when available, such as when the system is being used in a hospital or clinic setting. A coil or leaf spring 136 is fitted between the two outer plates 126, 128 to normally bias the unhinged ends of the bellows apart. Upon a downward pressure, the contents of the dual bladders 134 are forced out of one-way valves with air or $O_2$ delivered to the oxygenator 120 and blood being pumped to the heater 124 to be brought to body temperature. Upon release of pressure on the upper plate 128, the spring 136 elevates to draw air/oxygen from the reservoir 118 through the oxygenator 120 and to refill the blood bladder and completing one pump cycle. Alternative pumps, such as a battery-operated pump, may be employed. Other electric pumps may also be employed when it is anticipated that an electrical source will be readily available. The pump is adapted so that it may be powered manually by a health care provider repeatedly applying sufficient pressure to overcome the force of the spring 136 and then removing that pressure.

At the time of set up for use, it is imperative that no air bubbles be allowed to enter the patient's bloodstream to create an embolism. To avoid the problem, it is known to "prime" the circuit 114 by injecting normal saline solution through its blood carrying passages. It is a principal object of the present invention to provide a packaging method and apparatus for semiautomatically priming an ECMO/heart-lung machine circuit upon opening the container in which the ECMO/heart-lung machine circuit 114 of FIG. 14 is loaded at a time of manufacture.

Figure 15:
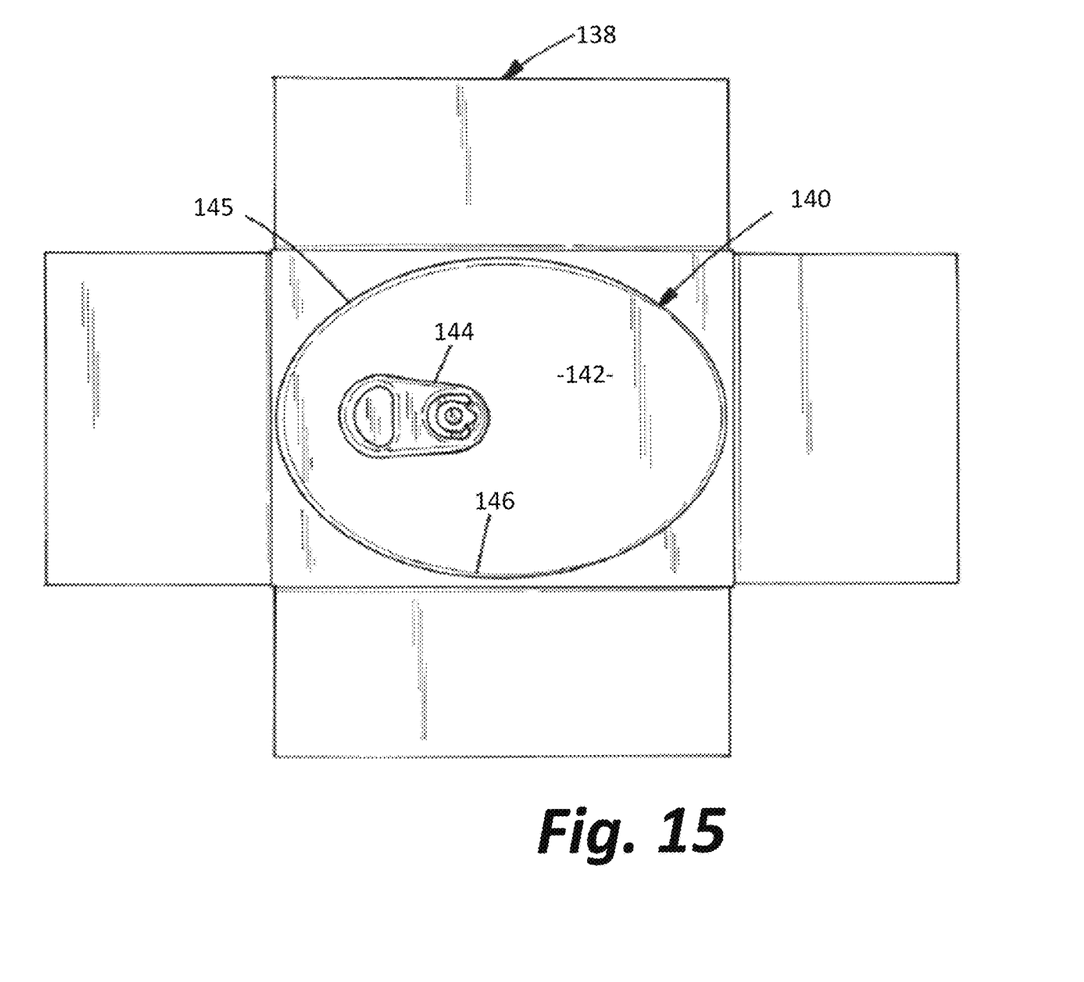
FIG. 15 is a plan view of a vacuum-packed container in which the ECMO/heart-lung machine circuit and bag of priming fluid is contained and located within a cardboard box for storage.

Referring to FIG. 15, there is shown the exterior packaging arrangement incorporating an outer carton/box 138 with its top flaps open to reveal a sealed metal outer container/can 140 in which the ECMO/heart-lung machine circuit is installed at a point of manufacture for long-term storage. The container is vacuum sealed and its lid 142 is adapted to be later opened by raising a pull ring 144 and removing the lid by tearing along a scored line 146 as is will be known in the food container arts. The box 138 allows items such as surgical supplies and personal protective equipment (PPE) for medical personnel involved in applying the ECMO/heart-lung machine circuit for use with the patient in the corner areas of the box.

Placed within the volume of the container 140 is a vacuum housing 145, preferably formed of an open cell foam, such as polyurethane foam, that is contained within an outer plastic film tubular sleeve 149. The foam may conform to the interior of the lid can but be disconnected from the lid. It is molded or otherwise formed to have a shelf 147. Disposed within the foam housing are the components of the ECMO/heart-lung machine circuit including the interconnecting tubing. Not seen in the plan view of FIG. 16 is the blood oxygenator 120 in that it is hidden from view, being located beneath the blood pump 122 in this view.

Figure 16:
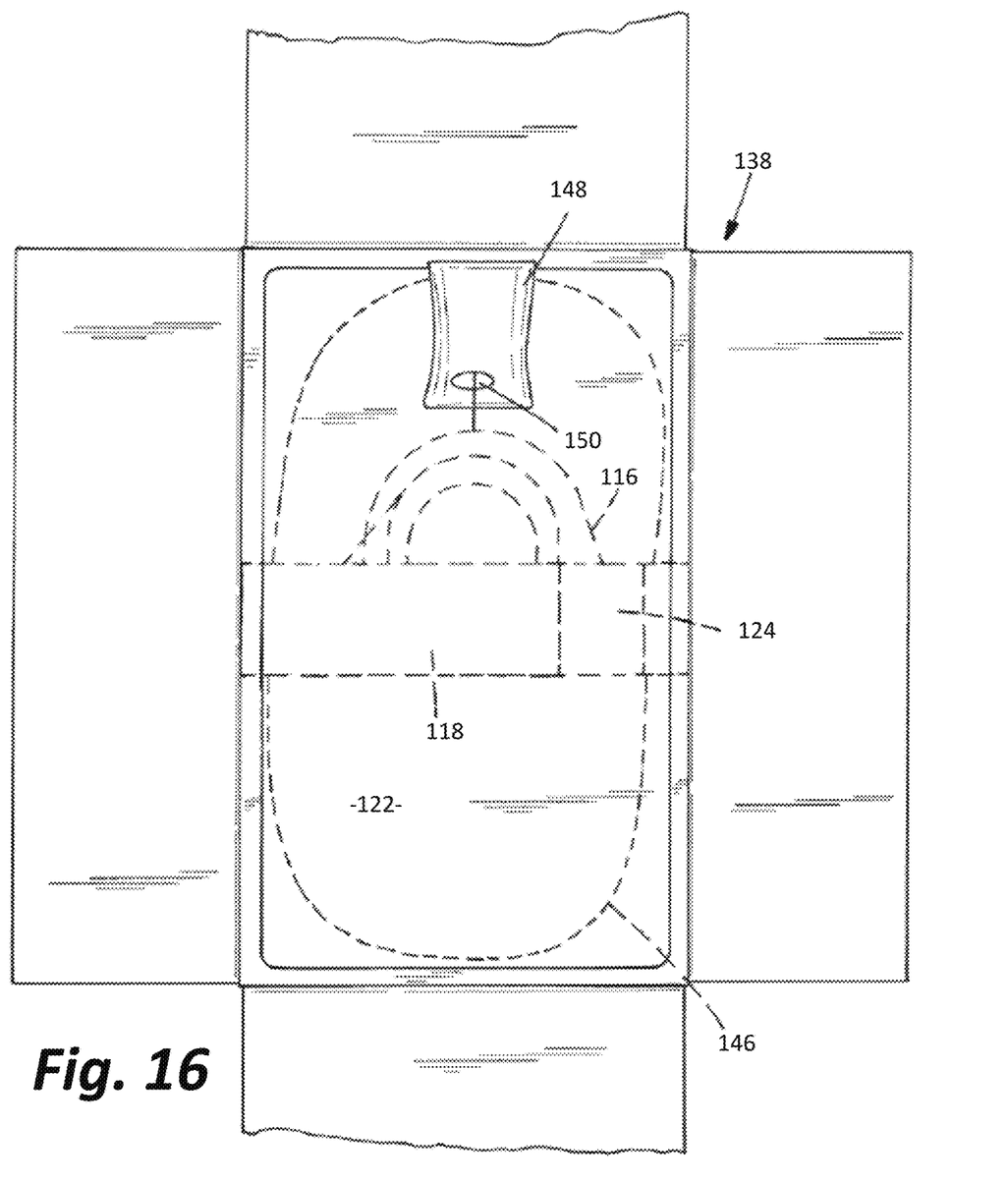
FIG. 16 is a top plan view showing the components of FIG. 14 contained within a molded foam housing.
Figure 17:
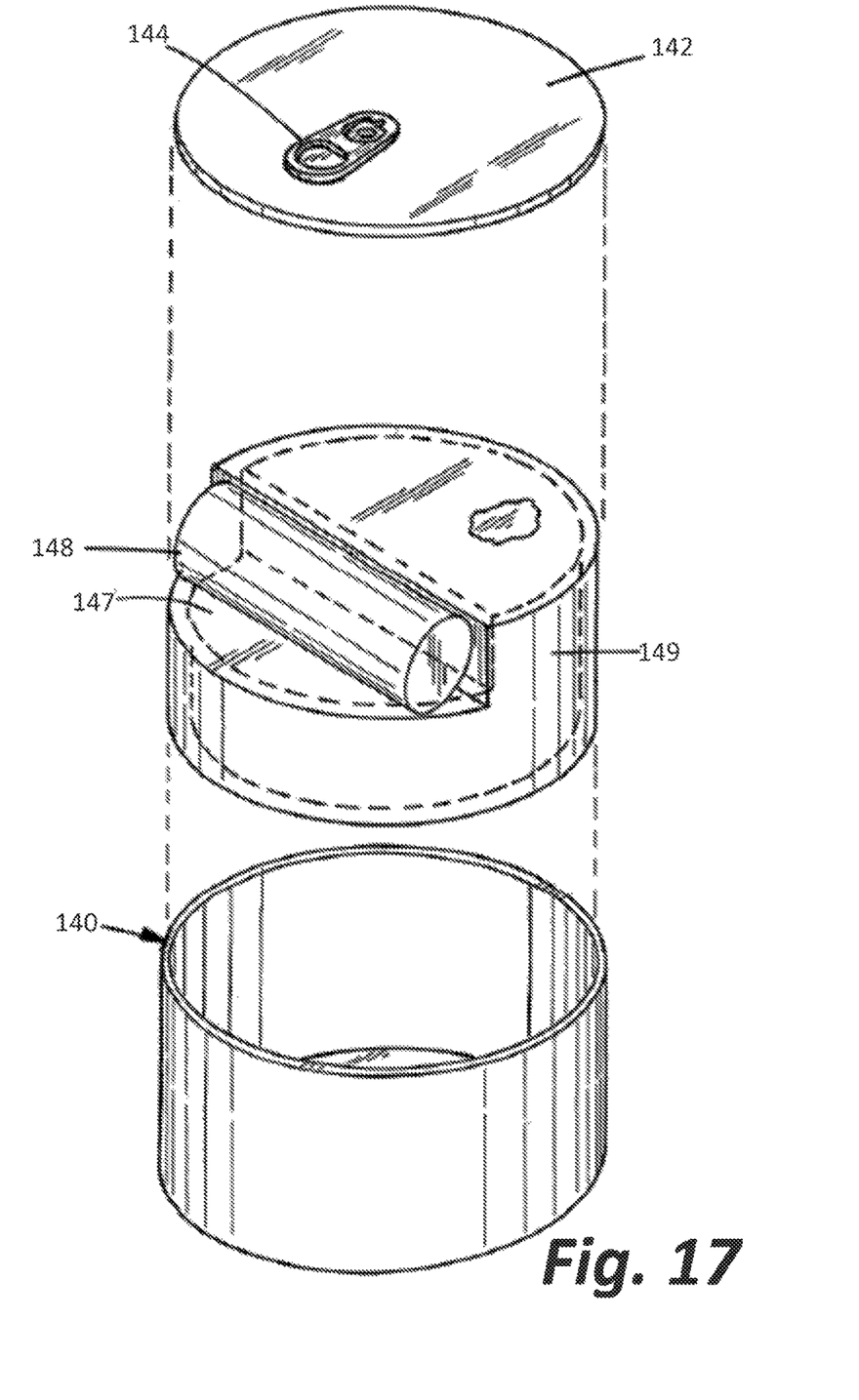
FIG. 17 is exploded view of an open cell foam housing assembly for containing the ECMO/heart-lung machine circuit components of FIG. 14 therein at the time of manufacture of the self-priming ECMO/heart-lung machine made in accordance with the present invention.

As seen in FIG. 16, located within the container 140, but exterior to the foam housing and resting on the shelf 147 is a flexible plastic bag 148 that is filled with normal saline. A connection is made through a normally closed pressure activated valve 150 to tubing leading to the reservoir 118.

Before the metal housing is sealed, it is flushed at the factory with carbon dioxide (CO2) to effectively eliminate traces of nitrogen (N2) that may be present in the room atmosphere. Upon attachment of the top 142 to the sidewalls of the container, a vacuum is drawn inside the container 140 to a range of from about 300 to 380 mm Hg, but limitation to this range is not intended. Following pump down and sealing of the metal container with all of the components of the ECMO/heart-lung machine circuit (except the bag of priming fluid 148) contained within the hollow open cell foam housing, the container can be packaged and sealed within the cardboard box 138 and stored on a shelf in a supply room of a medical facility or transported to a patient location by paramedic personnel who have had training in the cannulization of a patient on whom VVECMO, VAECMO or other use is indicated due to lung and heart failure.

At the time of use, the container 140 will be opened, thus exposing the bag of prime fluid 148 to atmospheric pressure. However, because the ECMO/heart-lung machine circuit is contained within the plastic film wrapped open cell foam housing 146, it remains at least momentarily at the earlier established negative pressure such that the pressure on the primed fluid bag will force open the valve 150 to allow the priming fluid to be drawn from its bag through the ECMO/heart-lung machine circuit 114 and thereby force any air from the components and the interconnecting tubing.

Atmospheric pressure acting on the prime fluid bag 148 to force fluid through the ECMO/heart-lung machine circuit can also be readily supplemented by manually squeezing the bag or by elevating the bag relative to the ECMO/heart-lung machine circuit allowing gravity to act and thereby fill the pump ventricle. Any carbon dioxide that may remain from the initial factory flushing step will be forced out of the circuit by the introduction of the priming fluid and is allowed to escape via strategically placed diffuser valves (not shown) that allow air to pass, but that block liquid. Such diffuser valves are preferably placed on the top surface of the reservoir 118 and on the uppermost surface of the blood oxygenator.

With the bellows pump (ventricle) 122 (FIG. 14) now filled with priming fluid, manual pedal pressure may be applied to the upper plate 128 of the bellows pump to squeeze the priming fluid (saline) through the heater 124 and into the patient who by this time has been cannulated. The patient's own venous pressure, as well as gravity due to the patient being elevated relative to the reservoir 118 and the blood oxygenator 120, will cause the patient's blood to displace the priming fluid as the blood pump is cyclically depressed and allowed to expand due to the force of the compression spring 136.

The blood is made to flow upward through the blood oxygenator 120 in that it is placed on its side with its membrane support plates disposed vertically. As such, any bubbles that might possibly be present are drawn off through the properly placed gas diffusers, thus tending to ensure that any microbubbles cannot accumulate and are not embolized. With the connections being such that blood enters the bottom of the oxygenator and out its top and upward into the pump's ventricle 134 (FIG. 14) and out to the heater 124 before re-entering the patient it will negate formation of air bubbles being carried into the patient.

It is further conceived that the bellows pump can be driven by any one of several commercially available respiratory ventilators rather than being manually oscillated. This offers the advantage that such ventilators incorporate sensors and controls for setting the pumping rate.

This invention has been described herein in considerable detail to comply with the patent statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

The invention claimed is:

1. A vacuum assisted self-priming heart-lung machine comprising (a) an outer container for holding an inner housing; (b) the inner housing comprising an open cell foam structure contained within a plastic film sleeve; (c) a heart-lung machine circuit disposed within the inner housing; (d) a compressible bag holding a quantity of priming fluid disposed in the outer container, wherein the compressible bag is external to the inner housing and connected through a pressure relief valve to the heart-lung machine circuit, said outer container being vacuum sealed at the time of manufacture to a predetermined negative pressure with respect to atmospheric pressure.

2. The vacuum assisted self-priming heart-lung machine of claim 1 wherein the heart-lung machine circuit comprises in combination a reservoir, a blood oxygenator, a pump, and a heater module connected in a serial fashion to one another by flexible plastic tubing.

3. The vacuum assisted self-priming heart-lung machine of claim 2 characterized in that opening of the outer container at a time of use exposes the compressible bag to atmospheric pressure to collapse the compressible bag and thereby force the priming fluid through the pressure relief valve and the heart-lung machine circuit to purge air from the heart-lung machine circuit.

4. The vacuum assisted self-priming heart-lung machine of claim 3 wherein the priming fluid comprises normal saline.

5. The vacuum assisted self-priming heart-lung machine of claim 2 wherein the pump has a first mode of operation in which the pump is powered manually and a second mode of operation in which the pump is powered electrically.

6. The vacuum assisted self-priming heart-lung machine of claim 2 wherein the pump is adapted to draw blood through the blood oxygenator.

7. The vacuum assisted self-priming heart-lung machine of claim 3 wherein the blood oxygenator comprises a stack of alternating membrane support plates and spacers and an elongated pleated semi-permeable membrane extending alternately around each support plate and spacer and channels for introducing a patient's blood on one side of the membrane in a space between two membrane layers and for introducing one of air and oxygen gas on an opposite side of the membrane in a space between the membrane and a support plate, said support plates and membrane being vertically oriented.

8. The vacuum assisted self-priming heart-lung machine of claim 1 further comprising a box adapted to contain the outer container.

* * * * *